United States Patent
Fairley et al.

(10) Patent No.: US 7,399,950 B2
(45) Date of Patent: Jul. 15, 2008

(54) CONFOCAL WAFER INSPECTION METHOD AND APPARATUS USING FLY LENS ARRANGEMENT

(75) Inventors: Christopher R. Fairley, San Jose, CA (US); Tao-Yi Fu, Fremont, CA (US); Bin-Ming Benjamin Tsai, Saratoga, CA (US); Scott A. Young, Sequel, CA (US)

(73) Assignee: KLA-Tencor Corporation, San Jose, CA (US)

(*) Notice: Subject to any disclaimer, the term of this patent is extended or adjusted under 35 U.S.C. 154(b) by 0 days.

(21) Appl. No.: 11/521,930

(22) Filed: Sep. 15, 2006

(65) Prior Publication Data

US 2007/0007429 A1 Jan. 11, 2007

Related U.S. Application Data

(63) Continuation of application No. 11/079,614, filed on Mar. 14, 2005, now Pat. No. 7,109,458, which is a continuation of application No. 09/533,203, filed on Mar. 23, 2000, now Pat. No. 6,867,406.

(60) Provisional application No. 60/125,568, filed on Mar. 23, 1999.

(51) Int. Cl.
G02B 7/04 (2006.01)

(52) U.S. Cl. .................................. 250/201.3

(58) Field of Classification Search ... 250/201.2–201.4; 356/609
See application file for complete search history.

(56) References Cited

U.S. PATENT DOCUMENTS

| | | | |
|---|---|---|---|
| 3,597,045 A | 8/1971 | Mathisen | |
| 4,634,880 A | 1/1987 | Lindow et al. | |
| 4,656,358 A | 4/1987 | Divens et al. | |
| 4,677,301 A | 6/1987 | Tanimoto et al. | |
| 4,683,524 A | 7/1987 | Ohta | |
| 4,707,610 A | 11/1987 | Lindow et al. | |

(Continued)

FOREIGN PATENT DOCUMENTS

EP 871052 A1 10/1998

*Primary Examiner*—Thanh X Luu
(74) *Attorney, Agent, or Firm*—Smyrski Law Group, A P.C.

(57) ABSTRACT

A semiconductor wafer inspection system and method is provided which uses a multiple element arrangement, such as an offset fly lens array. The preferred embodiment uses a laser to transmit light energy toward a beam expander, which expands the light energy to create an illumination field. An offset fly lens array converts light energy from the illumination field into an offset pattern of illumination spots. A lensing arrangement, including a first lens, a transmitter/reflector, an objective, and a Mag tube imparts light energy onto the specimen and passes the light energy toward a pinhole mask. The pinhole mask is mechanically aligned with the offset fly lens array. Light energy passing through each pinhole in the pinhole mask is directed toward a relay lens, which guides light energy onto a sensor. The offset fly lens array corresponds to the pinhole mask. The offset pattern of the offset fly lens array is chosen such that spots produced can be recombined into a continuous image, and the system utilizes a time delay and integration charge coupled device for rapid sensing along with an autofocus system that measures and cancels topological features of the specimen.

19 Claims, 8 Drawing Sheets

U.S. PATENT DOCUMENTS

| | | | |
|---|---|---|---|
| 4,717,242 A | 1/1988 | Echizen et al. |
| 4,732,473 A | 3/1988 | Bille et al. |
| 4,734,923 A | 3/1988 | Frankel et al. |
| RE32,660 E | 5/1988 | Lindow et al. |
| 4,789,222 A | 12/1988 | Ota et al. |
| 4,806,004 A | 2/1989 | Wayland |
| 4,806,774 A | 2/1989 | Lin et al. |
| 4,845,356 A | 7/1989 | Baker |
| 5,112,129 A | 5/1992 | Davidson et al. |
| RE33,956 E | 6/1992 | Lin et al. |
| 5,184,021 A | 2/1993 | Smith |
| 5,208,648 A | 5/1993 | Batchelder et al. |
| 5,220,403 A | 6/1993 | Batchelder et al. |
| 5,231,467 A | 7/1993 | Takeuchi et al. |
| 5,248,876 A | 9/1993 | Kerstens et al. |
| 5,264,912 A | 11/1993 | Vaught et al. |
| 5,276,498 A | 1/1994 | Galbraith et al. |
| 5,327,223 A | 7/1994 | Korth |
| 5,363,021 A | 11/1994 | MacDonald |
| 5,365,051 A | 11/1994 | Suzuki et al. |
| 5,377,001 A | 12/1994 | Malin et al. |
| 5,377,002 A | 12/1994 | Malin et al. |
| 5,389,794 A | 2/1995 | Allen et al. |
| 5,406,085 A | 4/1995 | Sharma |
| 5,479,252 A | 12/1995 | Worster et al. |
| 5,541,416 A | 7/1996 | Washizuka |
| 5,546,189 A | 8/1996 | Svetkoff et al. |
| 5,587,832 A | 12/1996 | Krause |
| 5,596,413 A | 1/1997 | Stanton et al. |
| 5,602,399 A | 2/1997 | Muzutani |
| 5,602,400 A | 2/1997 | Kawashima |
| 5,633,720 A | 5/1997 | Takahashi |
| 5,654,800 A | 8/1997 | Svetkoff et al. |
| 5,661,548 A | 8/1997 | Imai |
| 5,672,861 A * | 9/1997 | Fairley et al. ............ 250/201.3 |
| 5,728,495 A | 3/1998 | Ozawa |
| 5,737,084 A | 4/1998 | Ishihara |
| 5,854,674 A | 12/1998 | Lin |
| 6,043,932 A | 3/2000 | Kusunose |
| 6,091,488 A | 7/2000 | Bishop |
| 6,248,988 B1 | 6/2001 | Krantz |
| 6,867,406 B1 | 3/2005 | Fairley et al. |

* cited by examiner

CONFOCAL WAFER INSPECTION METHOD AND APPARATUS USING FLY LENS ARRANGEMENT

This application is a continuation of U.S. patent application Ser. No. 11/079,614, filed Mar. 14, 2005 now U.S. Pat. No. 7,109,458, entitled "Confocal Wafer Inspection Method and Apparatus," inventors Christopher R. Fairley, et al., which is a continuation of U.S. patent application Ser. No. 09/533,203, filed Mar. 23, 2000, "Confocal Wafer Inspection Method and Apparatus," inventors Christopher R. Fairley, et al., now U.S. Pat. No. 6,867,406, issued Mar. 15, 2005, and claims the benefit of the filing date of U.S. Provisional Patent Application No. 60/125,568, entitled "Confocal Wafer Inspection Method and Apparatus," filed Mar. 23, 1999, pursuant to 35 U.S.C. Sections 111 and 119(e), all of which are hereby incorporated by reference.

BACKGROUND OF THE INVENTION

1. Field of the Invention

The present invention relates generally to precision optical inspection methods for specimens such as semiconductor wafers, and more specifically to a method and apparatus for performing microscopic inspection and measurement of integrated circuit wafer geometries using laser confocal microscopy.

2. Description of the Related Art

In integrated circuit inspection, particularly inspection of semiconductor wafers or photomasks from which such circuits are fabricated, different methods have been employed to address particular characteristics of the wafers or advantages afforded by specific inspection technologies.

One such method that has previously been employed in semiconductor wafer or photomask inspection is confocal microscopy. Confocal imaging entails suppressing out of focus specimen elements at image formation. The suppression of out of focus elements occurs partially as a result of the specimen not being illuminated and imaged as a whole at one time, but as one point after another, and also due to the detection pinhole, or spatial filter, interposed between the source and specimen. The sequential point imaging in confocal microscopy is obtained using an arrangement of diaphragms which act as both a point source and a point detector simultaneously at optically coexistant points of the path of light rays used to inspect the specimen. Rays which are out of focus are suppressed by the detection pinhole.

Other inspection techniques have been employed with varying results. Non-confocal imaging tends to be highly sensitive to signals located outside the focal plane, which can add unwanted noise to the imaging process. Noise may also result from defect detection on a semiconductor wafer due to the various layers present on the wafer. Confocal imaging using light elements other than lasers have been employed, but such arrangements create illumination spots with inefficient and slow pinholes since the arc or filament cannot increase in intensity, due to limited power.

Laser confocal imaging addresses the drawbacks of these previous systems. An illustration of a typical laser confocal microscopy inspection arrangement for imaging a single point is illustrated in FIG. 1. Laser 101 emits a beam of light rays 102 which passes through a focusing lens 103 and subsequently through first spatial filter 104. After passing through confocal element 104 the light rays flare outward toward beamsplitter 105. Beamsplitter 105 allows the light rays to pass through and toward objective 106, which focuses the light rays toward the specimen. Light rays reflected from an object at the focal plane 107 pass back toward the objective 106 and beamsplitter 105. Beamsplitter 105 at this point reflects the light rays as illustrated toward second confocal element 108. Objects above or below the focal plane 107 are out of focus and are therefore suppressed. The remaining in focus light rays pass to detector 109.

The advantages of confocal microscopy include the feature that light rays from outside the focal plane are not registered. Confocal imaging can provide true three dimensional data recording, but instead gradually optically removes portions of the specimen as those portions move away from the focal plane. In practice, the elements tend to disappear from the field of view. Stray light tends to be minimized in a confocal arrangement.

The drawbacks associated with the arrangement of FIG. 1 are that the system shown therein only of confocal imaging include a limited field of view, typically a small point on the specimen. Thus scanning an entire specimen would require several passes even for moderately sized specimens. Speed and throughput tend to be of great importance during wafer inspection, and thus confocal techniques have been limited in their application.

Multiple scanning spot systems have been employed to increased inspection speed and throughput. These multiple scanning spot systems utilize mechanical polygon scanning spot laser arrangements to provide increased scanning areas. However, the mechanical polygon scanning techniques tend to be highly unstable and do riot provide necessary fine image alignment for comparison of adjacent features under most circumstances.

Certain confocal systems employ techniques for performing inspection of a wafer or specimen but each system has particular negative aspects. For example, U.S. Pat. No. 5,248,876 to Kerstens, et al., illustrates a confocal imaging system using an opaque mask having a slit and a row of pinpoint sensors or a skewed pattern of isolated pinholes with an array of isolated pinpoint sensors in a matching pattern. The problem with such an arrangement is the sensing of data. The Kerstens sensing arrangement employs an array 116 having isolated pinpoint radiation sensors 114. The problem with such a system is that it is inherently slow and, inefficient in scanning large amounts of data. In particular, the Kerstens system has a very limited dynamic range and can result in obscured or saturated parts of the image under normal inspection speeds.

The Kerstens system also uses a type of autofocus system which uses multiple confocal measurements to determine features on the surface of the system. In particular, the effective focus position of the Kerstens system is a function of the position on the wafer such that the geometry effects the ability of the system to focus on a particular feature and measuring the height of a particular feature.

Other known confocal inspection systems can have problems maintaining focus on a single layer in a multiple layer specimen, such as a CMP (Chemical Mechanical Planarization) specimen. On a multiple layer specimen, inspection of the topmost surface may be required, and certain systems employing confocal techniques do not provide the ability to discriminate or focus on the desired layer. Focusing becomes a problem due to decreasing line widths, desire for increased optical resolution, and a corresponding decrease in depth of focus. Most autofocus systems, such as the autofocus system presented in the Kerstens reference, see through the multiple layers on specimens such as CMP specimens to follow the underlying layers, resulting in non-planar focus performance having varying sensitivity to surface defects resulting from following the underlying topology.

It is therefore an object of the current invention to provide an inspection system which provides noise reduction in images received and the ability to control focus in a multiple depth environment, such as a CMP specimen, in particular with respect to signals which are out of the depth of focus and out of the depth of application interest of the system.

It is a further object of the current invention to provide a high speed and accurate brightfield and darkfield image inspection system without the speed, illumination, and processing drawbacks of traditional laser inspection systems or non-laser systems utilizing lamps.

It is another object of the current invention to provide an inspection system which minimizes the instabilities associated with mechanical scanning systems.

It is yet another object of the current system to provide a confocal system having the ability to inspect a comparatively large area at a relatively rapid rate with minimal distortion at a maximum dynamic range.

It is a further object of the current system to provide for a robust and effective focusing system for multiple layer specimens that is simple and has the ability to effectively discern and account for height differences within the specimen.

SUMMARY OF THE INVENTION

According to the present invention, there is provided a semiconductor wafer inspection system and method using a multiple element arrangement, such as an offset fly lens array. The preferred embodiment of the current system uses a laser to transmit light energy toward a beam expander, which expands the light energy from the laser beam to create an illumination field. The system uses an offset fly lens array to convert the light energy from the illumination field into an offset pattern of illumination spots. The offset pattern of illumination spots is transmitted to a first lens which focuses the array of light energy produced toward the surface of the wafer specimen. Light energy then passes through a transmitter/reflector which transmits the light energy toward the surface of the wafer specimen. Light energy from the transmitter/reflector passes through objective which provides an array of beams, rather than a single beam, onto the surface of the wafer specimen, and the image from the wafer surface is reflected back through the objective. Light energy passes toward transmitter/reflector, which reflects light energy toward a tube lens, which focuses the multiple beams toward a pinhole mask. The pinhole mask is mechanically aligned with the offset fly lens array according to an approximate tolerance. Light energy passing through each of the pinholes in the pinhole mask is directed toward a relay lens, which directs light energy onto a sensor, preferably a TDI CCD sensor. Other sensors may be used which permit receipt of light energy.

The offset fly lens array is preferably a 16 (X direction) by 128 (Y direction) element lens array, as is the corresponding pinhole mask. The offset pattern of the offset fly lens array is chosen and arranged such that the spots produced from the offset fly lens array can be recombined in the system into a continuous image by image sensor. Binary optics may be employed to create a darkfield illumination profile for each individual spot produced by the offset fly lens arrangement.

The TDI CCD sensor provides a relatively high dynamic range for scanning and provides the ability to scan a surface on the order of 500 times faster than previous systems. The implementation of the TDI CCD in the present system is adjacent to and preceded by a pinhole mask having similar pinhole dimensions as the offset fly lens array. The lensing arrangement, offset fly lens array, and the pinhole mask are arranged to provide an accurate image on the sensor based on the type of specimen being inspected. The offset fly lens array and the pinhole mask are mechanically well aligned to one another during system operation and scanning. Generally, the TDI CCD has an opaque surface, such as metal, located on the back of the ultraviolet TDI, with polysilicon on the front side of the TDI sensor. The polysilicon is opaque in the ultraviolet range.

One potential use of the system is in conjunction with a slit laser confocal arrangement. Also, the system may employ autofocus capabilities which must be kept stable for particular wafer specimens. Unstable autofocus may tend to cause severe signal variations and is generally unusable. In particular, the autofocus used in the present system ignores various layers rather than evaluating multiple confocal measurements and cancelling undesirable measurements. The process of ignoring layers not pertinent to the scan is that focus is more rapid and effective for multiple height measurements.

If the system uses a large NA (numerical aperture) objective, high angle darkfield can be employed in the system by using an aperture in a fourier plane. Confocal Z discrimination, inherent in confocal systems, reduces the necessity for providing both high angle of incidence and grazing angle dark field evaluation. In such a high angle dark field arrangement, the binary fly lens arrangement permits constructing efficient directional dark field spots for confocal imaging.

An alternate arrangement for dark field confocal imaging may use a UBB arc lamp to provide light energy to a beam compressor/expander which takes light energy from the multidirectional arc lamp and focuses the light energy from the arc lamp to create a broad illumination field. This embodiment employs a pinhole array to convert light energy from the broad illumination field into an offset pattern of illumination spots. The offset pattern of illumination spots is transmitted to a lens which focuses the array of light energy toward the surface of the wafer specimen. Light energy then passes through a transmitter/reflector which transmits the light energy toward the surface of the wafer specimen. Light energy from the transmitter/reflector passes through an objective which provides an array of beams, rather than a single beam, onto the surface of the wafer specimen, and the image from the wafer surface is reflected back through the objective. Light energy passes toward the transmitter/reflector, which reflects light energy toward a Mag tube. Mag tube focuses the multiple beams toward pinhole mask. The pinhole mask again must be mechanically aligned with the pinhole array to be within good mechanical alignment. Light energy passing through each of the pinholes in the pinhole mask is directed toward a relay lens, which directs light energy onto a sensor.

An alternate embodiment of the current invention is to use an AOD scanning system, which provides better mechanical stability over a mechanical polygon scanning system. This increases the stability provided by the fixed array of conjugate pinholes in the illumination and collection paths of the system.

Other objects, features, and advantages of the present invention will become more apparent from a consideration of the following detailed description and from the accompanying drawings.

DESCRIPTION OF THE DRAWINGS

FIG. 3b shows a combination of the three scan images of FIG. 3a;

DETAILED DESCRIPTION OF THE INVENTION

The inventive system disclosed herein employs multiple wavelength confocal inspection techniques in conjunction with an offset fly lens arrangement and a TDI CCD sensor. Multiple wavelength confocal inspection enhances the ability to obtain an extended focus image or enhanced surface profile information with a single scan, or the ability to scan at varying specimen depths while maintaining focus on the various depths during a single scan pass. The use of such techniques provides light to be transmitted at multiple wavelengths without crosstalk.

Figure 1:
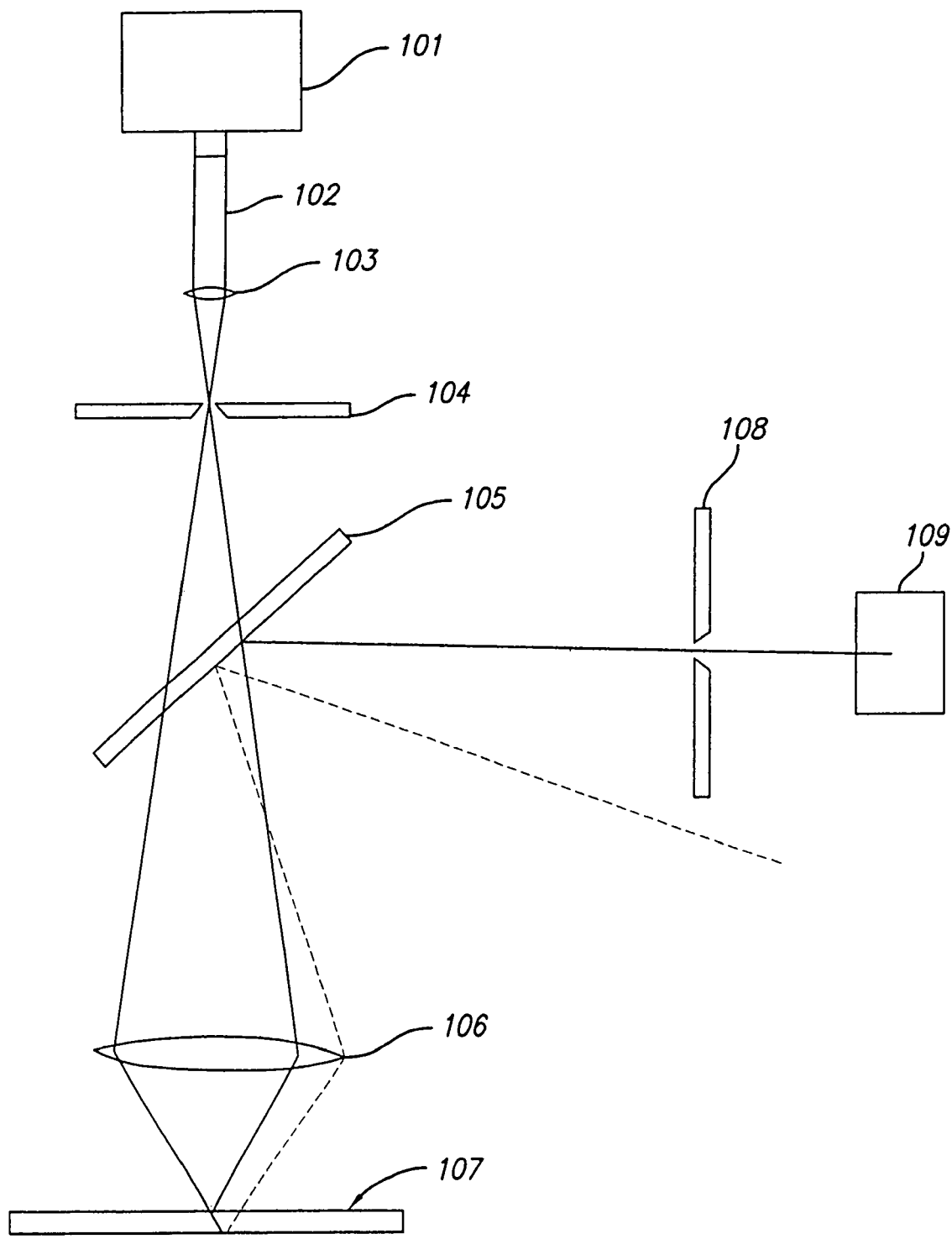
FIG. 1 illustrates a typical prior art laser confocal microscopy inspection arrangement.
Figure 2:
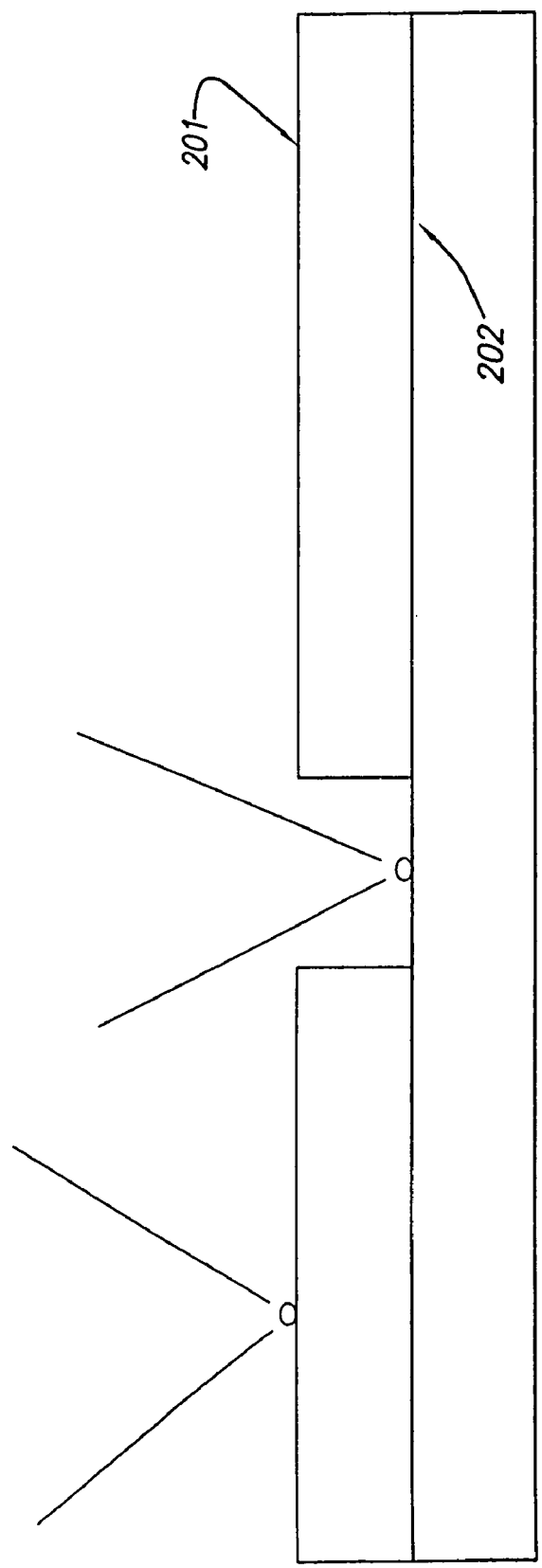
FIG. 2 presents a multilevel specimen which benefits from confocal inspection is a system using parallel processing of brightfield and darkfield data.

FIG. 2 illustrates a multilevel specimen which benefits from confocal inspection. A first scan frequency provides a focused image based on the topmost surface 201 of the specimen, while a second scan frequency provides a focused image based on a contact bottom 202 of the specimen. A further third scan frequency, not shown, provides a focused image based on the bottom surface of the specimen.

Figure 3A:
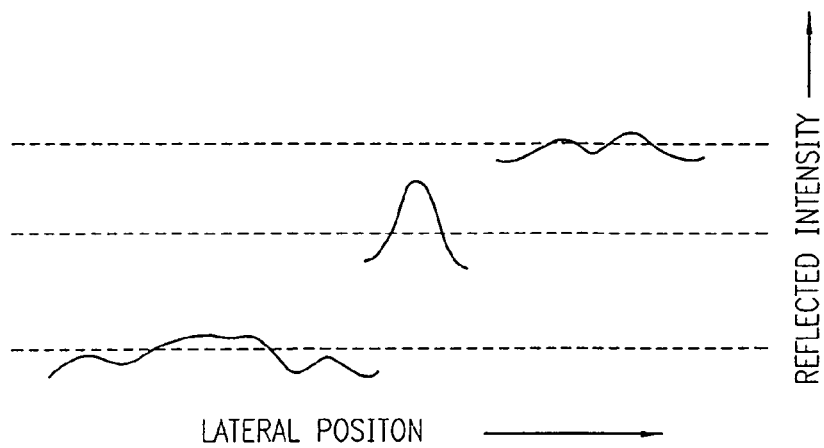
FIG. 3a is an illustration of three returns from the scan of the specimen illustrated in FIG. 2.
Figure 3B:
Figure 3C:
FIG. 3c illustrates the signal received by a sensor wherein pinholes are used to block out of focus portions of the signal.

The three returns from the scan of the specimen illustrated in FIG. 2 is presented in FIG. 3a, where the x coordinate of FIG. 3a represents the lateral position during the scan and the y coordinate represents the reflected intensity. A system employing confocal inspection for such a multilevel specimen then combines the scan images as shown in FIG. 3b, which represents the unfiltered return from the arrangement illustrated in FIG. 2. Pinholes are used to block any signal which is out of focus, resulting in the sensor receiving the signal shown in FIG. 3c.

Figure 4:
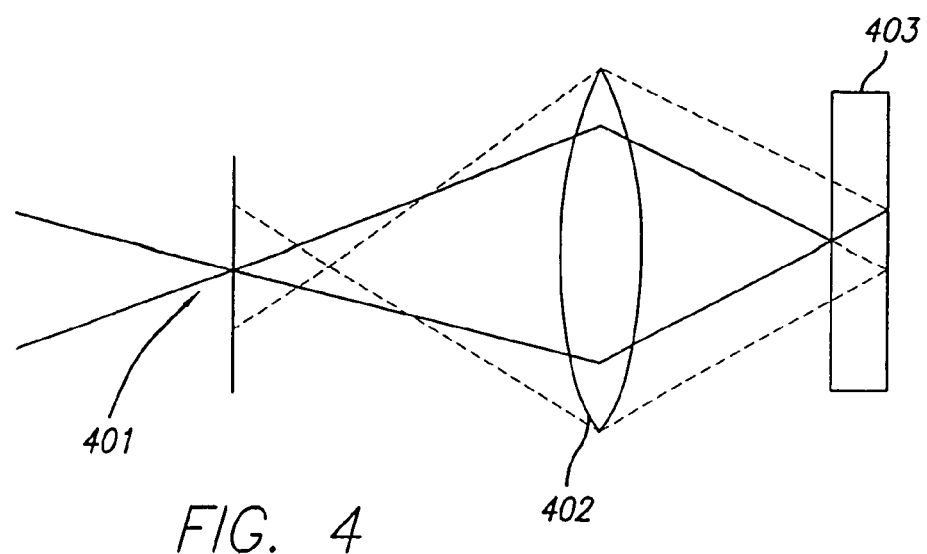
FIG. 4 illustrates the filtering of images using a confocal arrangement.

FIG. 4 illustrates the filtering of images using a confocal arrangement and the operation of the pinholes. The illuminator and sensor (both not shown) are located away from the pinhole 401, focusing lens 402, and wafer specimen 403. The illuminator transmits light through the pinhole 401 and toward the objective lens, or focusing lens 402. The focusing lens 402 provides focus of the light beams onto the wafer 403, here with the focal plane positioned on the leftmost illustrated, or top, surface of the wafer 403. Some light is transmitted through the top layer of the wafer as shown, reflecting off an interior layer at a particular angle and being directed toward focusing lens 402. Focusing lens 402 transmits the light energy as shown toward the pinhole 401, but as shown the out of focus rays are blocked by the spatial filter or pinhole. The light energy outside the pinhole diameter is out of focus, and only the focused, central light images pass through the pinhole and on toward the sensor.

Figure 5:
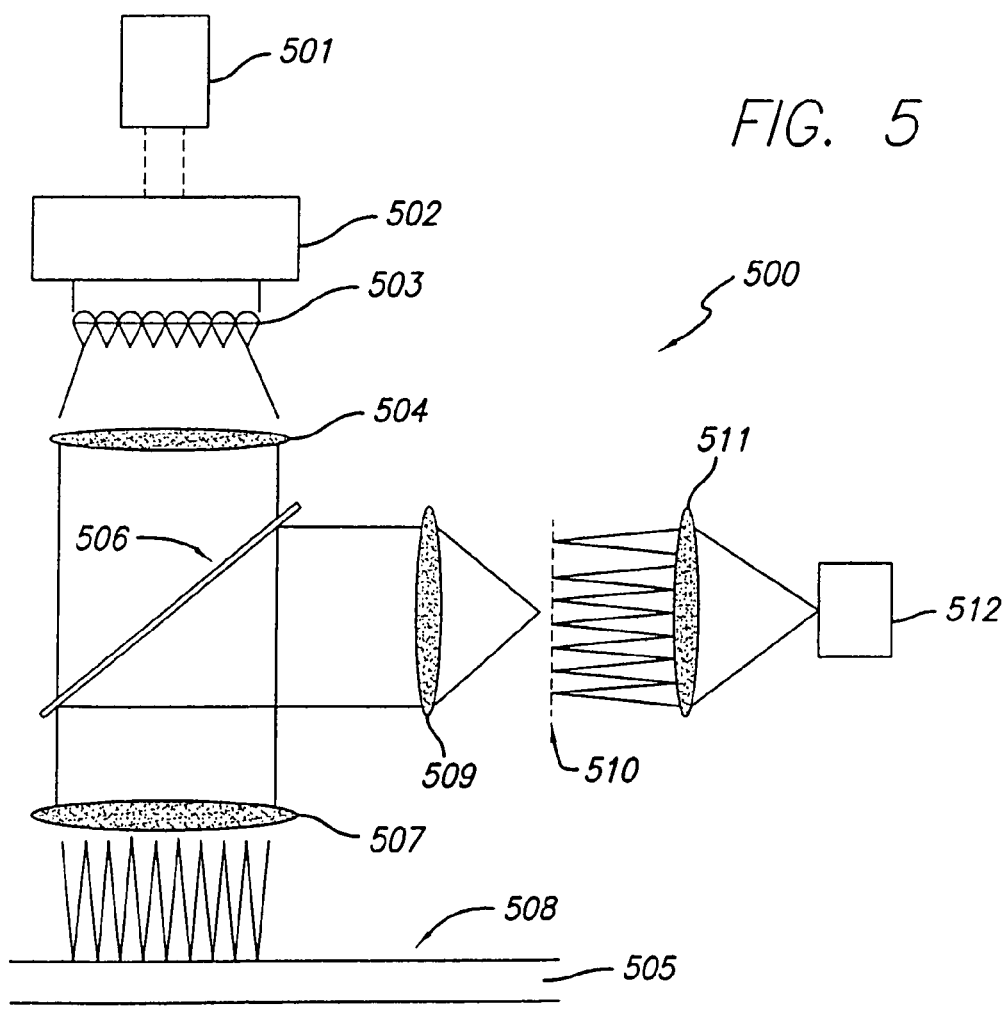
FIG. 5 presents the inventive system disclosed herein using an offset fly lens arrangement.

The inventive system 500 is illustrated in FIG. 5. Laser 501 transmits light energy toward a beam expander 502 which expands the light energy from the laser beam to create an illumination field. The system uses an offset fly lens array 503 to convert the light energy from the illumination field into an offset pattern of illumination spots. The offset pattern of illumination spots is transmitted to a first lens 504 which relays the array of light energy produced toward the surface of the wafer specimen 505. Light energy then passes through a transmitter/reflector 506 which transmits the light energy toward the surface 508 of the wafer specimen 505. Light energy from the transmitter/reflector 506 passes through objective 507 which provides an array of beams, rather than a single beam, onto the surface 508 of the wafer specimen, and the image from the wafer surface 508 is reflected back through objective 507. If a surface of specimen 505 is within one of the spots transmitted thereupon, the radiation is reflected back from said specimen 505 and through the system 500. Light energy passes toward transmitter/reflector 506, which reflects light energy toward focusing tube 509. Focusing tube 509 focuses the multiple beams toward pinhole mask 510. The pinhole mask 510 must be mechanically aligned with the offset fly lens array 503 as described below. Light energy passing through each of the pinholes in the pinhole mask 510 is directed toward relay lens 511, which directs light energy onto sensor 512. Sensor 512 is preferably a TDI sensor, but other sensors may be used which permit receipt of light energy.

Figure 6:
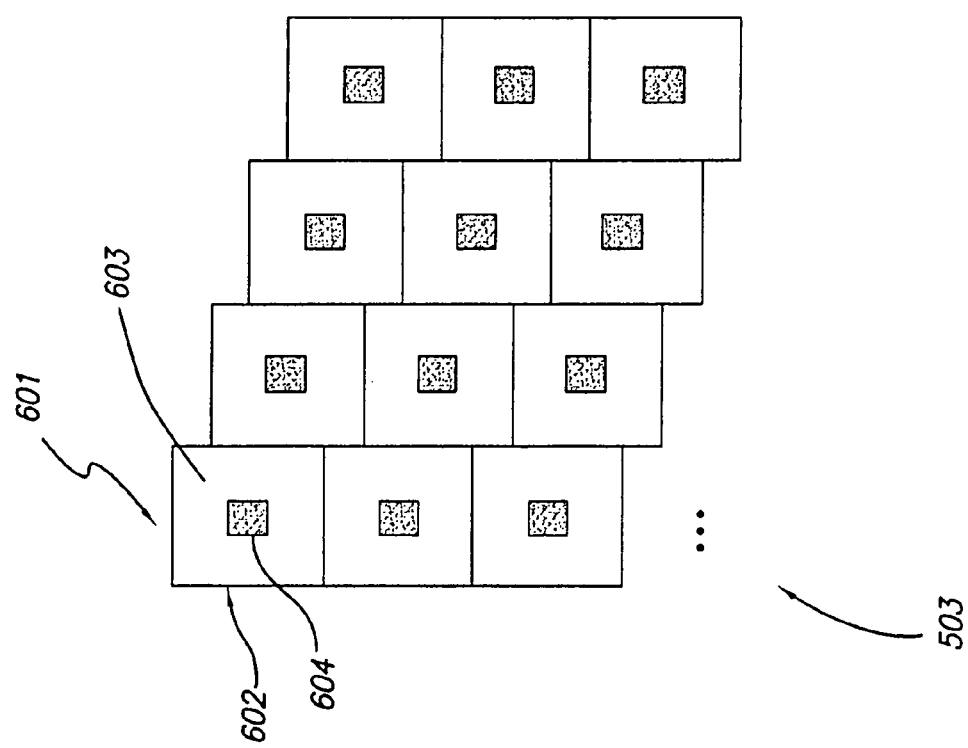
FIG. 6 is a section of the offset fly lens array.

FIG. 6 illustrates a portion of the offset fly lens array 503. Preferably the offset fly lens array 503 is a 16 (X direction) by 128 (Y direction) element array of lenses. A lens element 601 comprises an exterior edge 602, an interior portion 603, and a central pixel grouping 604, with each central pixel grouping 604 comprising 16×16 pixels. The pinhole mask 16×128 pinhole arrangement, providing a one-to-one correspondence between the lens elements and the holes in the pinhole mask. The offset pattern of the offset fly lens array 503 is chosen and arranged such that the spots produced from the offset fly lens array 503 can be recombined in the system into a continuous image by image sensor 512. Binary optics (not shown) may be employed to create a darkfield illumination profile for each individual spot produced by the offset fly lens arrangement 503. Such profiles could include bright field illumination, dark field illumination, and/or directional dark field illumination. The binary optics are used to construct an inexpensive fly lens array having uniform or non uniform illumination profiles which can improve overall signal to noise ratio of defect detection.

A wafer stage (not shown) affords the system the ability to move the wafer specimen 505 beneath the spots produced to provide the ability to image any and all portions of the wafer specimen. An imaging optics train (not shown) images the spots onto the pinhole mask 510. The pinhole mask 510 has the same offset pattern and alignment as the offset fly lens array 503. Preferably the system 500 of FIG. 5 does not include any moving parts apart from the stage transporting the specimen.

Alternative arrangements to that shown in FIG. 5 may be used. For example, the pinhole array may be located on the TDI sensor or be separate from the sensor and the pinhole array may use a relay lens for confocal in/out selectability. Generally speaking, the lensing arrangement and the offset fly lens array 503 and the pinhole mask 510 must be carefully arranged to provide an accurate image on the sensor. The offset fly lens array 503 and the pinhole mask 510 must be in mechanical alignment with one another during system operation and scanning.

One potential alternate use of the system is in conjunction with a slit laser confocal arrangement. Also, the system may employ autofocus capabilities which must be kept stable for particular wafer specimens. Unstable autofocus may tend to cause severe signal variations in the arrangement illustrated in FIG. 5. In the present system, spots or areas of interest on the specimen surface may be located at different heights, i.e. at varying distances from the objective 507. The ability to discern features on specimens having varying heights is provided by the following autofocus system. First, the system receives the information from the area of interest including height measurements and data at the particular heights. Thus the instrument detects the topological features of the specimen as the specimen passes along the path of scanning.

Figure 8:
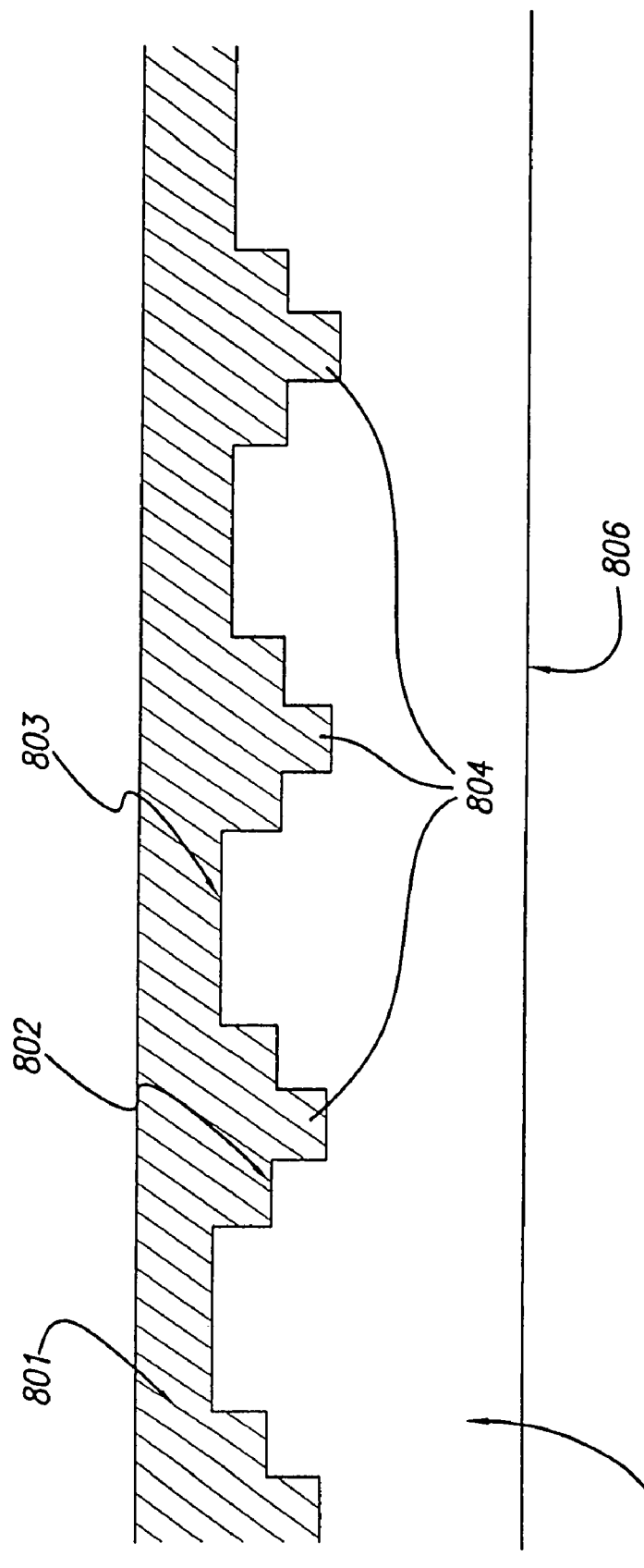
FIG. 8 illustrates a cross section of the topology of a typical wafer specimen.

An example of a cross section of a wafer specimen is presented in FIG. 8. The cross section of FIG. 8 is typical for a memory device having a central memory array surrounded by peripheral circuitry such as row/column decoders. The arrangement disclosed in FIG. 8 represents such a specimen at an intermediate stage of fabrication, including dielectric 801, peripheral circuitry (first metal layer) 802, memory array (second metal layer) 803, streets 804, underlying silicon 805, and a backside area 806. During scanning, the resultant focus position will vary across the die because the illumination used for focus "sees" the underlying metal and silicon topology.

Generally the system applies an offset to the autofocus system to provide as much in-focus viewing over the entire die area. The current autofocus system measures variations across a specimen, records the variations, and cancels the variations during inspection, thus maintaining a planar focus condition. During scanning, die or specimen rows are swathed with the autofocus system responding to the topology present within the swathing field of view. Swaths frequently overlap one another to account for variations in topology in paths perpendicular to the direction of scanning. The system maps the focus profile for the entire specimen, and it is preferable to have a single focus profile. Therefore the system bottom adjusts the swathing to avoid height variations in neighboring elements. In operation, the system scans the die and records the focus profile. Several die may be averaged to remove noise and wafer tilt by equalizing end points of the focus scan.

Figure 9:
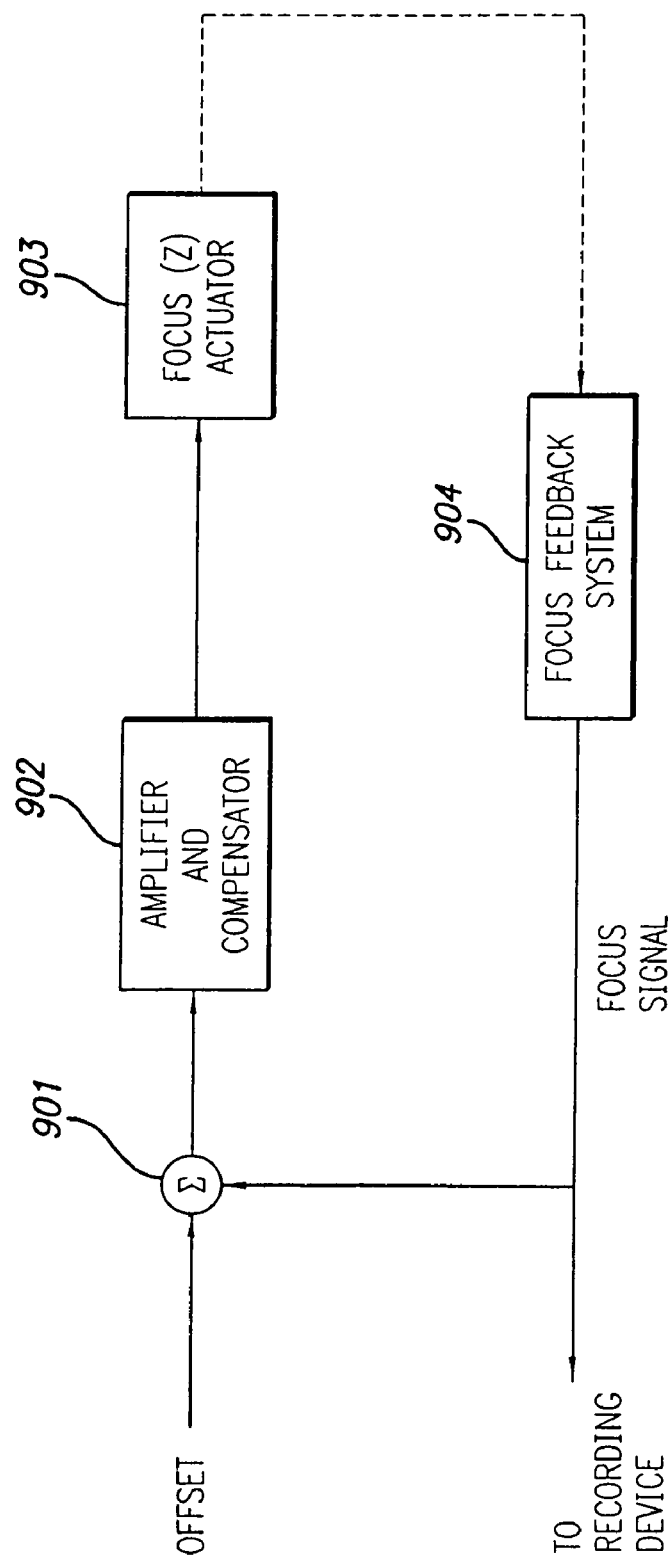
FIG. 9 is a schematic of the control system for providing autofocus using cancellation.

The addition of an offset is shown in the block diagram of FIG. 9. FIG. 9 shows that planar autofocus is effectuated by holding the focus actuator at a static position, wherein the system records the focus signal across each swath of the die. During inspections, the focus profile is replayed into the autofocus control loop to cancel the effect of the underlying topology. This canceling aspect provides a planar focus condition at a height which is not necessarily that of the top surface of the wafer. The system applies a further DC offset either electronically or optically to select the top surface. In FIG. 9, the offset is sent into summing element 901, which is applied to amplifier and compensator 902 and to focus actuator 903. A typical system includes an amplifier and compensator and may include an actuator for dynamic focus. In the present system, focus feedback is provided via focus feedback system 904, which feeds the system focus signal to summing element 901 and back to the recording element for recording the depth measurements.

With respect to the pinhole mask 510 used in the current system, the apertures in pinhole mask 510 are preferably the size of or smaller than the diffraction limit of the radiation generated. Further, the aperatures are separated from one another by at least several times the diffraction limit to minimize the potential for stray radiation. The pattern of apertures is selected such that every point of the viewed surface moves through an illuminated spot corresponding to the spots on the mask. The view of the spots on the specimen is recorded and the recorded data is processed to generate a complete image of the specimen. Pinhole offset is not necessarily equal to pinhole width, and pinholes may overlap to provide redundancy.

Images are acquired by scanning the object along the path and reading an output from the TDI sensor each time the object moves by a predetermined width, for example the width of one pixel.

If the system uses a large NA (numerical aperture) objective, high angle darkfield can be employed in the system by using an aperture in a fourier plane. When high incidence angle darkfield evaluation is employed in conjunction with a binary fly lens arrangement, the binary fly lens arrangement allows construction of efficient directional dark field spots for confocal imaging. The presence of confocal Z discrimination, inherent in confocal systems, can reduce the need for high incidence angle (grazing angle) dark field evaluation.

Figure 7:
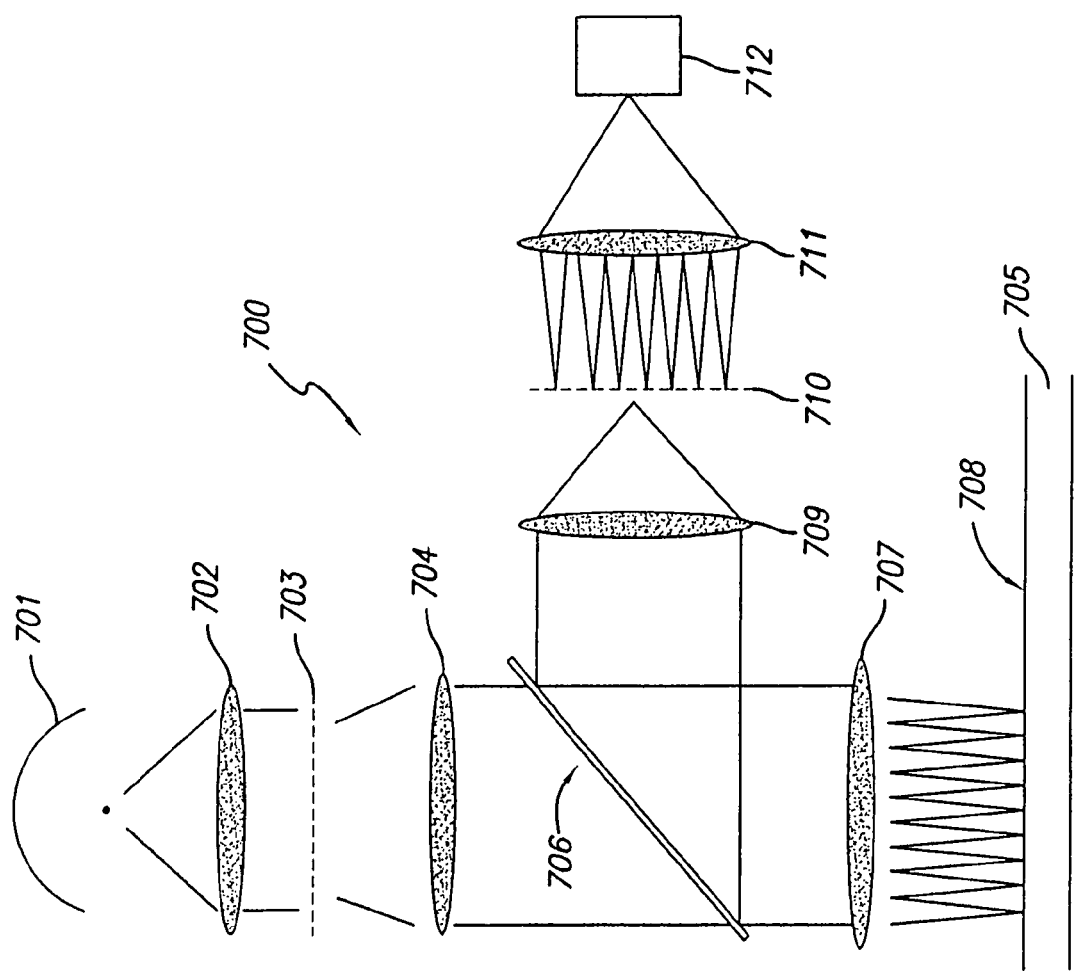
FIG. 7 presents an alternate arrangement of the current system for use with dark field confocal imaging.

An alternate arrangement for dark field confocal imaging is presented in FIG. 7. As shown therein, a UBB arc lamp 701 provides light energy to a beam compressor/expander 702 which receives the light energy transmitted by the omnidirectional arc lamp 701 and expands the light energy to create a broad illumination field. The system employs a pinhole array 703 to convert light energy from the broad illumination field into an offset pattern of illumination spots. The offset pattern of illumination spots is transmitted to a lens 704 which focuses the array of light energy toward the surface of the wafer specimen 705. Light energy then passes through a transmitter/reflector 706 which transmits the light energy toward the surface of the wafer specimen 705. Light energy from the transmitter/reflector 706 passes through objective 707 which provides an array of beams, rather than a single beam, onto the surface 708 of the wafer specimen, and the image from the wafer surface 708 is reflected back through objective 707. Light energy passes toward transmitter/reflector 706, which reflects light energy toward Mag tube 709. Mag tube 709 focuses the multiple beams toward pinhole mask 710. The pinhole mask 710 again must be mechanically aligned with the pinhole array 703 to be within plus or minus one micrometer mechanical alignment. Light energy passing through each of the pinholes in the pinhole mask 710 is directed toward relay lens 711, which directs light energy onto sensor 712. Sensor 712 is preferably a TDI sensor, but again, other sensors may be used which permit receipt of light energy. As with the embodiment illustrated in FIG. 5, an alternate to the relay lens 711 is to place the pinhole mask on the surface of the sensor 712. The TDI sensor assembles the final image based on the array of spots. The result is a wider swath of the image is viewed in a single pass, thereby decreasing throughput without image degradation.

The construction of sensor 712 when employing a TDI CCD sensor is as follows. First, the pinhole mask 710 is located adjacent the TDI sensor, either directly in contact with the sensor or spaced a short distance from the sensor 712. The back of the TDI sensor is constructed of an opaque material, such as a metal, with polysilicon preferably located on the front side of the detector and forming the pinhole mask. The polysilicon is also opaque in the ultraviolet range.

An alternate embodiment of the current invention is to use an AOD scanning system, which provides better mechanical stability over a mechanical polygon scanning system.

While the invention has been described in connection with specific embodiments thereof, it will be understood that the invention is capable of further modifications. This application is intended to cover any variations, uses or adaptations of the invention following, in general, the principles of the invention, and including such departures from the present disclo-

We claim:

1. A system for inspecting a specimen comprising an autofocus control loop, the autofocus control loop configured to receive an offset and comprising:
   a focal actuator configured to dynamically set system focus partially based on the offset; and
   a summing element configured to sum dynamically set system focus and offset to produce a value;
   wherein said focus signal is provided to a recording device and employed to cancel topology effects encountered in inspecting said specimen.

2. The system of claim 1, wherein said focal actuator provides signals through a focus feedback system to the recording device.

3. The system of claim 1, further comprising an amplifier and compensator that receive the value, amplify and compensate the value, and provide the amplified and compensated value in the form of the system focus to the summing element.

4. The system of claim 1, wherein the system comprising the autofocus control loop further comprises:
   means for performing an initial scan to determine specimen depth features;
   means for determining a bottom depth on the specimen and setting a bottom inspection threshold at the bottom depth; and
   means for performing a feature scan of the specimen using the bottom inspection threshold and wherein the autofocus control loop modulates focus depth based on the initial scan, the offset, the means for dynamically setting, and the means for dynamically summing.

5. A method for inspecting a specimen using an autofocus control loop, the autofocus control loop configured to receive an offset and the method comprising:
   dynamically setting focus parameters at least partially based on the offset; and
   summing dynamically set focus parameters and offset to produce summation output;
   wherein said inspecting of the specimen employs the summation output and the offset to a recording device to cancel topology effects encountered while inspecting the specimen.

6. The method of claim 5, wherein dynamically setting comprises providing signals through a focus feedback system to recording device.

7. The method of claim 5, further comprising receiving the summation output, amplifying and compensating the summation output, and providing the amplified and compensated summation output in the form of the focus parameters to the-summing element.

8. The method of claim 5, further comprising:
   performing an initial scan to determine specimen depth features;
   determining a bottom depth on the specimen and setting a bottom inspection threshold at the bottom depth; and
   performing a feature scan of the specimen using the bottom inspection threshold and modulating focus depth based on the initial scan, the offset, the dynamically setting, and the dynamically summing.

9. The method of claim 8, wherein performing the initial scan comprises performing multiple inspection swaths across the specimen.

10. The method of claim 9, wherein the specimen comprises a semiconductor wafer.

11. The method of claim 10, wherein the semiconductor wafer comprises:
    at least one metal layer; and
    silicon underlying the at least one metal layer.

12. The method of claim 8, wherein said method maintains a relatively planar focus condition.

13. The method of claim 8, further comprising scanning additional specimens and equalizing resultant feature scans.

14. The method of claim 13, wherein equalizing resultant feature scans comprises averaging specimen values thereby removing noise and tilt.

15. A system for inspecting a specimen, the system employing an autofocus control loop configured to receive an offset and comprising:
    means for dynamically setting system focus partially based on the offset; and
    means for summing dynamically set system focus and offset to produce an error;
    wherein the system focus is provided to a recording device and employed with the summing means to cancel topology effects encountered in inspecting said specimen.

16. The system of claim 15, wherein said dynamic setting means provides signals through a focus feedback system to the recording device.

17. The system of claim 15, further comprising an amplifier and compensator that receive the error, amplify and compensate the error, and provide the amplified and compensated error in the form of the system focus to the summing element.

18. The system of claim 15, wherein the system comprising the autofocus control loop further comprises:
    means for performing an initial scan to determine specimen depth features;
    means for determining a bottom depth on the specimen and setting a bottom inspection threshold at the bottom depth; and
    means for performing a feature scan of the specimen using the bottom inspection threshold and wherein the autofocus control loop modulates focus depth based on the initial scan.

19. The system of claim 18, wherein the inspection system comprises a fly lens arrangement, and performing the initial scan and performing the feature scan employ the fly lens arrangement.

* * * * *